United States Patent
Bartel et al.

(10) Patent No.: US 6,278,013 B1
(45) Date of Patent: Aug. 21, 2001

(54) OPTIONALLY SUBSTITUTED 8-CYANO-1-CYCLOPROPYL-7-(2,8-DIAZABICYCLO[4.3.0]NONAN-8-YL)-6-FLUORO-1,4-DIHYDRO-4-OXO-3-QUINOLINECARBOXYLIC ACIDS AND THEIR DERIVATIVES

(75) Inventors: Stefan Bartel, Bergisch Gladbach; Thomas Jaetsch, Köln; Thomas Himmler, Odenthal; Hans-Georg Rast, Bergisch Gladbach; Werner Hallenbach, Monheim; Ernst Heinen, Echternacherbrück; Franz Pirro, Langenfeld; Martin Scheer, Wuppertal, all of (DE); Michael Stegemann, Kansas City, MO (US); Hans-Peter Stupp; Heinz-Georg Wetzstein, both of Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/718,062

(22) Filed: Nov. 21, 2000

Related U.S. Application Data

(62) Division of application No. 09/125,191, filed on Aug. 13, 1998.

(30) Foreign Application Priority Data

Feb. 23, 1996 (DE) .............................................. 196 06 762
Aug. 22, 1996 (DE) .............................................. 196 33 805

(51) Int. Cl.$^7$ .................................................. C07C 255/50
(52) U.S. Cl. ............................................. 558/415; 558/416
(58) Field of Search ....................................... 558/415, 416

(56) References Cited

U.S. PATENT DOCUMENTS

| 5,140,033 | 8/1992 | Schriewer et al. ................... 514/312 |
| 5,252,734 | 10/1993 | Schriewer et al. ..................... 544/64 |

*Primary Examiner*—Bruck Kifle
(74) *Attorney, Agent, or Firm*—Joseph C. Gil; Godfried R. Akorli

(57) ABSTRACT

Intermediates useful in the preparation of 8-cyano-1-cyclopropyl-7-(2,8-diazabicyclo[4.3.0]nonan-8-yl-6-fluoro1,4-dihydro-4-oxo-3-quinolinecarboxylic acids of the following structures are claimed.

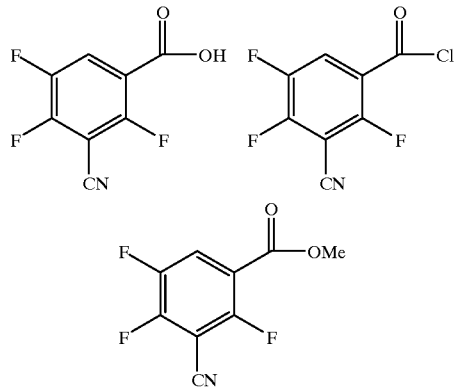

3 Claims, No Drawings

OPTIONALLY SUBSTITUTED 8-CYANO-1-CYCLOPROPYL-7-(2,8-DIAZABICYCLO[4.3.0]NONAN-8-YL)-6-FLUORO-1,4-DIHYDRO-4-OXO-3-QUINOLINECARBOXYLIC ACIDS AND THEIR DERIVATIVES

This is a Divisional application of Ser. No. 09/125,191, filed Aug. 13, 1998.

The present invention relates to novel optionally substituted 8-cyano-1-cyclopropyl-7-(2,8-diazabicyclo[4.3.0]nonan-8-yl)-6-fluoro-1,4-dihydro-4-oxo-3-quinolinecarboxylic acids and their derivatives, processes for their preparation and antibacterial compositions comprising them.

Quinolinecarboxylic acids and their antibacterial action have already been disclosed. Thus, ofloxacin, norfloxacin, enrofloxacin and danofloxacin are active compounds from this class of substance which are widely used in veterinary medicine. However, their use is not always satisfactory.

The present invention relates to optionally substituted 8-cyano-1-cyclopropyl-7-(2,8-diazabicyclo[4.3.0]nonan-8-yl)-6-fluoro-1,4-dihydro-4-oxo-3-quinolinecarboxylic acids and their derivatives, of the general formula (I)

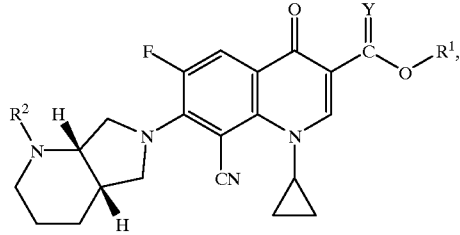

(I)

in which
- $R^1$ represents hydrogen, $C_1$–$C_4$-alkyl which is optionally substituted by hydroxyl, methoxy, amino, methylamino or dimethylamino, or (5-methly-2-oxo-1,3-dioxol-4-yl)methyl,
- $R^2$ represents hydrogen, benzyl, $C_1$–$C_3$-alkyl, (5-methyl-2-oxo-1,3-dioxol-4-yl)methyl, radicals having the structures —CH=CH—COOR$^3$, —CH$_2$CH$_2$COOR$^3$, —CH$_2$CH$_2$CN, —CH$_2$CH$_2$COCH$_3$ or —CH$_2$COCH$_3$, in which $R^3$ represents methyl or ethyl, or a radical of the general structure $R^4$—(NH—CHR$^5$—CO)$_n$—, in which $R^4$ represents hydrogen, $C_1$–$C_3$-alkyl or the radical —COO-tert-butyl, $R^5$ represents hydrogen, $C_1$–$C_4$-alkyl, hydroxyalkyl, aminoalkyl, thiloalkyl, carboxyalkyl or benzyl and n is 1 or 2, and
- Y is oxygen or sulfur.

The compounds of the formula (I) can be present in the form of racemates or as enantiomerically pure compounds, and in the form of their pharmaceutically usable hydrates and acid addition salts, as well as in the form of their alkali metal, alkaline earth metal, silver and guanidinium salts.

The present invention relates to the process for the preparation of optionally substituted 8-cyano-1-cyclopropyl-7-(2,8-diazabicyclo[4.3.0]nonan-8-yl)-6-fluoro-1,4-dihydro-4-oxo-3-quinolinecarboxylic acids, which is characterized in that compounds of the formula (II)

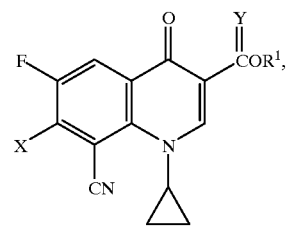

(II)

in which
- $R^1$ and Y have the abovementioned meaning and
- X represents halogen, in particular fluorine or chlorine, are reacted with 2,8-diazabicyclo[4.3.0]nonanes of the formula (III)

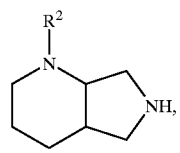

(III)

in which
- $R^2$ has the abovementioned meaning, if appropriate, in the presence of acid-binding agents. If appropriate, the carboxylic acid ester is then cleaved. If appropriate, compounds of the formula (I) in which $R^2$ represents hydrogen are then N-alkylated, N-alkenylated or N-acylated.

Compared with known representatives of this structural type, the compounds according to the invention have a more potent antibacterial action, in particular against *E. coli*, Staphylococci, Streptococci, Salmonellae and Mycoplasma. They are therefore suitable as active compounds for human and veterinary medicine. Their rapid degradation in the soil after excretion by the treated organism is advantageous.

Preferred compounds of the formula (I) are those in which
- $R^1$ represents hydrogen, $C_1$–$C_4$-alkyl which is optionally substituted by hydroxyl, methoxy, amino, methylamino or dimethylamino, or (5-methyl-2-oxo-1,3-dioxol-4-yl) methyl,
- $R^2$ represents hydrogen, benzyl, $C_1$–$C_3$-alkyl, (5-methyl-2-oxo-1,3-dioxol-4-yl)methyl, radicals of the structures —CH=CH—COOR$^3$, —CH$_2$CH$_2$COOR$^3$, —CH$_2$CH$_2$CN or —CH$_2$COCH$_3$, in which $R^3$ represents methyl or ethyl, or a radical of the general structure $R^4$—(NH—CHR$^5$—CO)$_n$—, in which $R^4$ represents hydrogen, $C_1$–$C_3$-alkyl or the radical —COO-tert-butyl, $R^5$ represents hydrogen, $C_1$–$C_4$-alkyl, hydroxyalkyl, aminoalkyl, thioalkyl or benzyl and n is 1 or 2, and
- Y represents oxygen, and pharmaceutically usable hydrates and acid addition salts thereof, as well as the alkali metal, alkaline earth metal, silver and guanidinium salts of the carboxylic acids on which the compounds are based.

Particularly preferred compounds of the formula (I) are those in which
- $R^1$ represents hydrogen, $C_1$–$C_4$-alkyl or (5-methyl-2-oxo-1,3-dioxol-4-yl)methyl,
- $R^2$ represents hydrogen, methyl, (5-methyl-2oxo-1,3-dioxol-4-yl)methyl, radicals of the structures —CH=CH—COOR$^3$, —CH$_2$CH$_2$COOR$^3$, —CH$_2$CH$_2$CN or —CH$_2$COCH$_3$, in which R$^3$ represents methyl or ethyl, or a radical of the general structure R$^4$—(NH—CHR$^5$—CO)$_n$—, in which R$^4$ represents hydrogen, C$_1$-C$_3$-alkyl or the radical —COO-tert-butyl, R$^5$ represents hydrogen, C$_1$-C$_4$-alkyl, hydroxyalkyl, aminoalkyl, thioalkyl or benzyl and n is 1 and 2, and Y represents oxygen,
and pharmaceutically usable hydrates and acid addition salts thereof, as well as the alkali metal, alkaline earth metal, silver and guanidinium salts of the carboxylic acids on which the components are based.

If, for example, 7-chloro-8-cyano-1-cyclopropyl-6-fluoro-1,4-dihydro-4-oxo-3-quinolinecarboxylic acid and 2,8-diazabicyclo[4.3.0.]nonane are used for the preparation of compounds of the formula (I), the course of the reaction can be represented by the following equation:

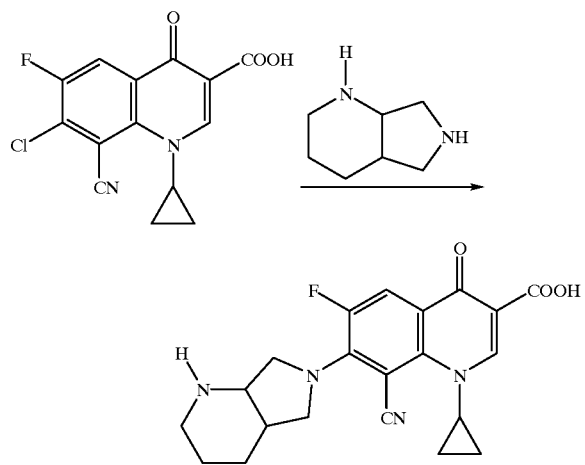

Compounds of the formula (I) can also be obtained be a procedure in which, after the reaction of a compound of the formula (II) with 2,8-diazabicyclo[4.3.0]nonane, a further reaction of the resulting product is carried out. Thus, compounds of the formula (I) where R$^2$ is a radical —CH=CH=COOEt, for example, can be obtained is accordance with the following equation:

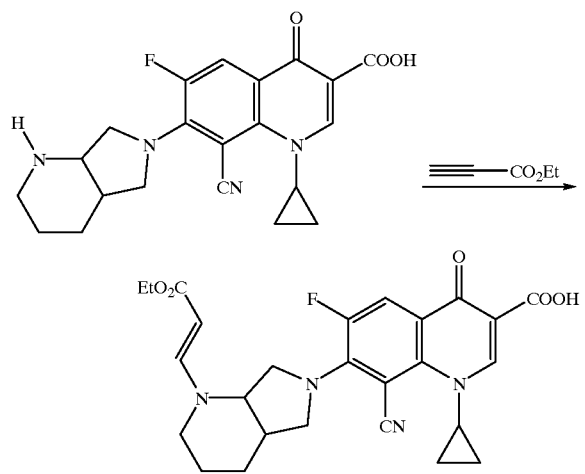

Compounds of the formula (I) in which R$^1$ represents hydrogen can be N-alkylated, N-alkenylated or N-acylated in a manner known per se.

For the N-alkylation, the alkyl halides or hydroxides corresponding to the radical R$^2$ or the alkenyls corresponding to the radical R$^2$ are used.

For the N-alkenylation, the alkinyls corresponding to the radical R$^2$ are used.

For the N-acylation, the acyl halides, in particular chlorides, or anhydrides corresponding to the radical R$^2$ are used.

Alkyl halides which may be mentioned are: benzyl chloride, C$_{1-3}$-alkyl iodides, bromides or chlorides, methyl or ethyl chloroethanecarboxylate and chiloroacetone;

alkenyls or alkinyls which may be mentioned are: methyl or ethyl propinylcarboxylate, ethyl acrylate and acrylonitrile; and acyl halides or anhydrides which may be mentioned are: acetyl chloride, pivaloyl chloride and N-tert-butyloxycarbonyl-L-alanine N-carboxyanhydride.

The N-alkylation with alkyl halides is preferably carried out in a diluent, such as, for example, dimethyl sulfoxide, N,N-dimethylformamide, sulfolane or acetonitrile.

Acid-binding agents which can be used are the customary inorganic and organic acid-binding agents, such as, for example, alkali metal hydroxides, alkali metal carbonates or organic amines.

The reaction temperatures can be varied within a substantial range here. The reaction is in general carried out between 20 and 200° C., preferably between 50 and 150° C.

The N-alkylation with alkenyls corresponding to the radical R$^2$ and the N-alkenylation with alkinyls corresponding to the radical R$^2$ are preferably carried out in a diluent, such as, for example, dimethyl sulfoxide, N,N-dimethylformamide, N-methyl-pyrrolidone, glycol, methylglycol or diethylene glycol.

The reaction temperatures can be varied here in a substantial range. In general, the reaction is carried out between 20 and 200° C., preferably between 50 and 180° C.

The N-acylation with acylhalides or anhydrides corresponding to the radical R$^2$ is preferably carried out in a diluent, such as, for example, dimethyl sulfoxide, N,N-dimethylformamide, sulfolane or N-methylpyrrolidone.

The reaction can be carried out without an acid-binding agent or also in the presence of such an agent.

Acid-binding agents which can be employed are the customary inorganic and organic acid-binding agents, such as, for example, triethylamine, 1,4-diaxabicyclo[2.2.2] octane and diazabicyclo[5.4.0]undec-7-ene.

The reaction temperatures can be varied within a substantial range here. In general, the reaction is carried out between −10° C. and 200° C., preferably between 0 and 150° C.

The compounds of the formula (II) used as starting compounds are known from U.S. Pat. No. 4,990,517 or can be prepared by known processes. Examples which may be mentioned are:
7-chloro-8-cyano-1-cyclopropyl-6-fluoro-1,4-dihydro-4-oxo-3-quinolinecarboxylic acid
methyl 7-chloro-8-cyano-1-cyclopropyl-6-fluoro-1,4-dihydro-4-oxo-3-quinolinecarboxylate
8-cyano-1-cyclopropyl-6,7-difluoro-1,4-dihydro-4-oxo-3-quinolinecarboxylic acid
ethyl 8-cyano-1-cyclopropyl-6,7-difluoro-1,4-dihydro-4-oxo-3-quinolinecarboxylate Thus, the compounds of the formula (II) can be prepared, for example, by reacting a compound of the formula (IV) with a β-dimethylamino-acrylic acid ester of the formula (V) and reacting the resulting product of the formula (VI) with cyclopropylamine to give a compound of the formula (VII), and then obtaining then compound (II):

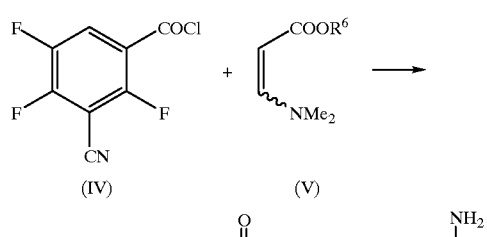

(IV)     (V)

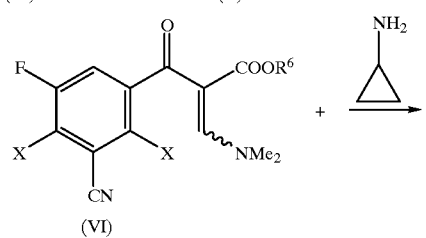

(VI)

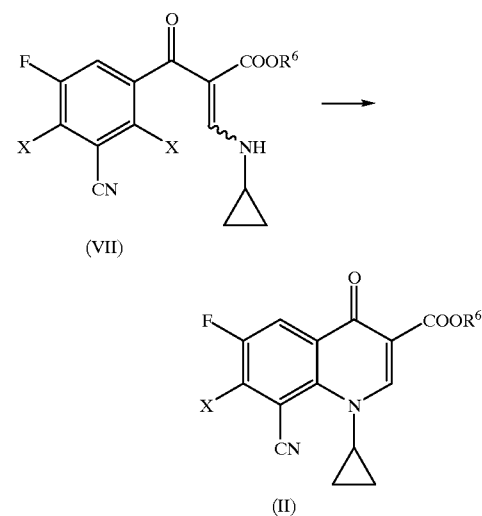

(VII)

(II)

In the above equation,

X represents halogen, in particular fluorine or chlorine, and $R^6$ represents $C_{1-4}$-alkyl, in particular methyl or ethyl, which is optionally substituted as described for $R^1$.

It is also possible to react a compound of the formula (IV) directly with a β-cyclopropylamino-acrylic acid ester:

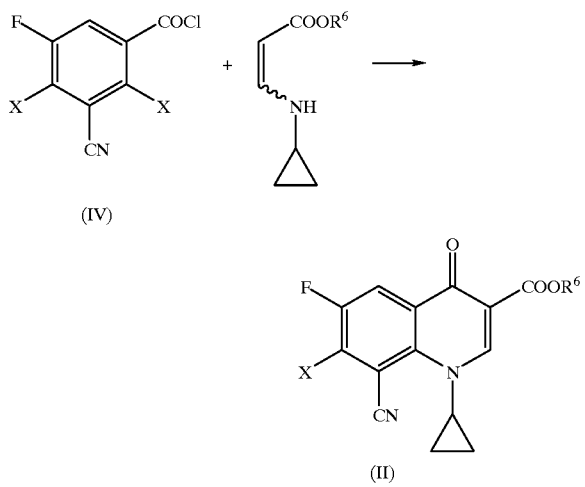

(IV)

(II)

(In the formulae, X and $R^6$ have the abovementioned meaning.)

In this case, the intermediate product, for example, of the formula (IV) where X=F can be prepared in accordance with the following equation:

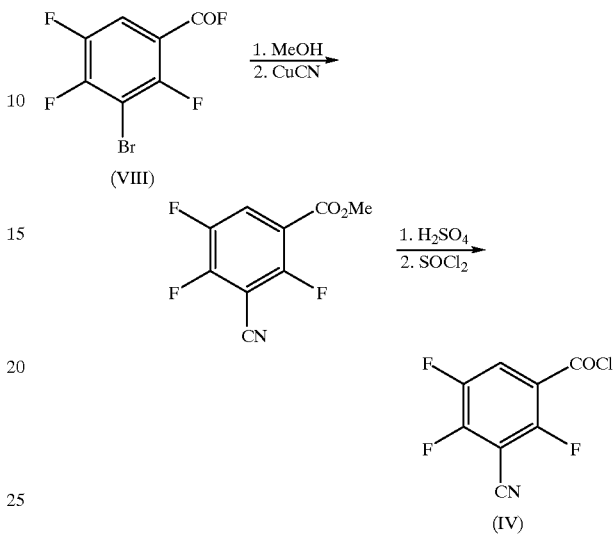

(VIII)

(IV)

The starting material of the formula (VIII) is known from DE 3 631 906.

The reaction of compounds of the formula (II) with compounds of the formula (III), in which the compounds (III) can also be employed in the form of their salts, such as, for example, the hydrochlorides, is preferably carried out in a diluent, such as dimethyl sulfoxide, N,N-dimethylformamide, N-methylpyrrolidone, hexamethylphosphoric acid trisamide, sulfolane, acetonitrile, water, an alcohol, such as methanol, ethanol, n-propanol or isopropanol, glycol monomethyl ether or pyridine. Mixtures of these diluents can also be used.

Acid-binding agents which can be used are all the customary inorganic and organic acid-binding agents. These include, preferably, the alkali metal hydroxides, alkali metal carbonates, organic amines and amidines. Particularly suitable agents which may be mentioned specifically are: triethylamine, 1,4-diazabicyclo[2.2.2]-octane (DABCO), 1,8-diazabicyclo[5.4.0]undec-7-ene (DBU) or excess amine (III).

The reaction temperatures can be varied within a substantial range. In general, the reaction is carried out between about 0 and 200° C., preferably between 20 and 180° C.

The reaction can be carried out under normal pressure, but also under increased pressure. In general, then reaction is carried out under pressures of between 1 bar and 100 bar, preferably between 1 and 10 bar.

In carrying out the process according to the invention, 1 to 15 mol, preferably 1 to 6 mol, of the compound (III) are employed per mole of the compound (II).

Free amino groups can be protected by a suitable amino-protective group, for example by the tert-butoxycarbonyl radical, during the reaction and, when the reaction has ended, liberated again by treatment with a suitable acid, such as hydrochloric acid or trifluoroacetic acid (see Houben-Weyl, Methoden der Organischen Chemie [Methods of Organic Chemistry], Volume E4, page 144 (1983); and J. F. W. McOmie, Protective Groups in Organic Chemistry (1973), page 43).

The esters according to the invention can also be obtained by reaction of an alkali metal salt of the carboxylic acid on which they are based, which can optionally be protected on the N atom by a protective group, such as the tert-butoxycarbonyl radical, with suitable halogenoalkyl derivatives in a solvent, such as dimethylformamide, dimethylacetamide, N-methylpyrrolidone, dimethyl sulfoxide or tetramethylurea, at temperatures of about 0 to 100° C., preferably 0 to 50° C.

The acid addition salts of the compounds according to the invention are prepared in the customary manner, for example by dissolving the betaine in an adequate amount of aqueous acid and precipitating the salt with a water-miscible organic solvent, such as methanol, ethanol, acetone or acetonitrile. It is also possible to heat equivalent amounts of betaine and acid in water or an alcohol, such as glycol monoethyl ether, and then to evaporate the mixture to dryness or to filter off the salt which has precipitated with suction. Pharmaceutically usable salts are to be understood as meaning, for example, the salts of hydrochloric acid, sulfuric acid, acetic acid, glycolic acid, lactic acid, succinic acid, citric acid, tartaric acid, methanesulfonic acid, 4-toluenesulfonic acid, galacturonic acid, gluconic acid, embonic acid, glutamic acid or aspartic acid. The compounds according to the invention can furthermore be bonded to acid or basic ion exchangers.

Acid addition salts of the compounds according to the invention can also be obtained by hydrolyzing a carboxylic acid ester of the formula (I), where $R^1$ is, for example, methyl or ethyl, with an adequate amount of the corresponding acid to give a carboxylic acid of the formula (I) where $R^1$ is hydrogen, and isolating the acid addition salt.

The alkali metal or alkaline earth metal salts of the carboxylic acids according to the invention are obtained, for example, by dissolving the betaine in less than the equivalent amount of alkali metal or alkaline earth metal hydroxide solution, filtering off the undissolved betaine and evaporating the filtrate to dryness. Sodium, potassium or calcium salts are pharmaceutically suitable. The corresponding silver salts are obtained by reaction of an alkali metal or alkaline earth metal salt with a suitable silver salt, such as silver nitrate.

Alkali metal or alkaline earth metal salts of the carboxylic acids according to the invention can also be obtained by hydrolyzing a carboxylic acid ester of the formula (I), where $R^1$ is, for example, methyl or ethyl, with an adequate amount of alkali metal or alkaline earth metal hydroxide solution and isolating the corresponding alkali metal salt or alkaline earth metal salt.

The compounds according to the invention have a potent antibiotic action and show a broad antibacterial spectrum against Gram-positive and Gram-negative germs, in particular also against those which are resistant to various antibiotics, such as, for example, penicillins, cephalosporins, aminoglycosides, sulfonamides and tetracyclines, coupled with a low toxicity.

These valuable properties enable them to be used as chemotherapeutic active compounds in medicine and veterinary medicine and as substances for preserving inorganic and organic materials, in particular all types of organic materials, for example polymers, lubricants, paints, fibres, leather, paper and wood, and foodstuffs and water.

The compounds according to the invention are active against a very broad spectrum of microorganisms. With the aid of these compounds, Gram-negative and Gram-positive bacteria and bacteria-like microorganisms can be controlled and the diseases caused by these pathogens can be prevented, alleviated and/or cured.

The compounds according to the invention are distinguished by an intensified action, above all, on resistant germs and Mycoplasma.

The compounds according to the invention show surprising increases in action against bacteria which are classified as less sensitive to comparable substances, in particular resistant Staphylococcus aureus and *E. coli*.

The compounds according to the invention are particularly active against bacteria and bacteria-like microorganisms. They are therefore particularly suitable in human and veterinary medicine for prophylaxis and chemotherapy of local and systemic infections caused by these pathogens.

The compounds are furthermore suitable for combating protozoonoses and helminthoses.

The compounds according to the invention can be used in various pharmaceutical formulations. Preferred pharmaceutical formulations which may be mentioned are tablets, coated tablets, capsules, pills, granules, suppositories, injection solutions, suspensions and emulsions and solutions, suspensions and emulsions which can be administered orally, and furthermore pastes, ointments, gels, creams, lotions, powders and sprays.

The active compounds are preferably suitable for combating bacterial diseases which occur in animal husbandry and animal breeding in stock, breeding, zoo, laboratory and test animals and pets, and have a favorable toxicity toward warm-blooded animals. They are active here against all or individual stages of development and against resistant and normally sensitive strains. By combating the bacterial diseases, disease, cases of death and reductions in productivity (for example production of meat, milk, wool, hides, eggs, honey and the like) should be diminished, so that more economical and easier animal husbandry is possible by the use of the active compounds.

The stock and breeding animals include mammals, such as, for example, cattle, horses, sheep, pigs, goats, camels, buffalo, donkeys, rabbits, fallow deer, reindeer, fur-bearing animals, such as, for example, mink, chinchillas and raccoons, and birds, such as, for example, chickens, geese, turkeys, ducks, pigeons and species of birds to be kept as pets and in zoos. They also include stock and ornamental fishes.

The laboratory and test animals include mice, rats, guinea pigs, golden hamsters, dogs and cats.

The pets include dogs and cats.

In general, it has proved advantageous to administer amounts of about 0.5 to about 50 mg, preferably 1 to 20 mg, of active compound per kg of body weight per day to achieve effective results.

The active compounds can also be administered to the animals together with the feed or drinking water.

Feed- and foodstuffs comprise 0.01 to 100 ppm, preferably 0.5 to 50 ppm, of the active compound, in combination with a suitable edible material.

Such a feed- and foodstuff can be used both for healing purposes and for prophylactic purposes.

Such a feed- or foodstuff is prepared by mixing a concentrate or a premix, which comprises 0.5 to 30%, preferably 1 to 20% by weight of an active compound mixed with an edible organic or inorganic carrier, with customary feedstuffs. Edible carriers are, for example, corn flour or corn and soybean flour or mineral salts, which preferably comprise a small amount of an edible dust prevention oil, for example maize oil or soya oil. The premix obtained here can then be added to the complete feedstuff before it is fed to the animals.

The minimum inhibitory concentrations (MIC) of the compounds according to the invention were determined by series dilution methods on Iso-Sensitest agar (Oxoid). For each test substance, a series of agar plates which contained concentrations of the active compound decreasing by double dilution in each case was prepared. The agar plates were inoculated with a Multipoint inoculator (Denley). Overnight cultures of the pathogens, which were diluted beforehand such that each inoculation point comprised about $10^4$ colony-forming particles, were used for the inoculation. The inoculated agar plates were incubated at 37° C. and the germ (growth was read after about 20 hours. The MIC value (µg/ml) indicates the lowest active compound concentration at which no growth was detectable with the naked eye. The MIC values for Mycoplasma were recorded under a microscope after an incubation period of 5 to 7 days.

The MIC values of one of the compounds according to the invention are shown in the following table in comparison with enrofloxacin, as the reference compound.

TABLE 1

MIC values (µg/ml)

| Species | Strain | Example 1 | Enrofloxacin |
|---|---|---|---|
| E. coli | Ec 9658 | 0.004 | 0.03 |
| Salmonella spp. | S 9659 | 0.06 | 0.5 |
| Pseudomonas aeruginosa | P 9503 | 0.25 | 1.0 |
| Bordetella bronchiseptica | B 9610 | 0.125 | 0.5 |
| Actinobacilius pleuropneumoniae | App 06/94 | 0.008 | 0.06 |
| Stapllylococcus aureus | St 2941 | 0.015 | 0.125 |
| Streptococcus agalactiae | Scc 9549 | 0.03 | 0.5 |
| Streptococcus suis | Scc 9593 | 0.06 | 0.5 |
| Actinomyces pyogenes | Am 9602 | 0.25 | 1.0 |
| Mycoplasma bovis | M 9548 | 0.015 | 0.25 |
| Mycoplasma iowae | M 95144 | 0.06 | 0.5 |
| Mycoplasma hyorhinis | M 9557 | 0.004 | 0.06 |
| Fusobacterium necrophorum | Ao 9620 | 0.03 | 4.0 |
| Clostridium perfringens | CI 9606 | 0.25 | 4.0 |

The improved pharmacokinetic properties of the substance from Example 1 according to the invention compared with the reference compound enrofloxacin was demonstrated on dogs in a serum kinetics study. The substances were tested in a dosage of 5 mg/kg of body weight on in each case 6 dogs of the beagle breed. The intravenous (i.v.), intramuscular (i.m.) and oral modes of administration were used in a simple cross-over design. It could be demonstrated with all the modes of administration that a higher peak value of the serum concentration ($C_{max}$), a longer half-life ($t_{1/2}$) and a longer residence time (MRT) is achieved with the substance from Example 1 according to the invention and thus a larger amount of substance is available in the organism (area under the serum level curve, $AUC_{0-24}$).

TABLE 2

Pharmacokinetic data

| | Example 1 | | | Enrofloxacin | | |
|---|---|---|---|---|---|---|
| | i.v. | i.m. | oral | i.v. | i.m. | oral |
| $C_{max}$ [µg/ml] | / | 2.4 | 1.3 | 1 | 2.1 | 1.0 |
| t½ [h] | 10.5 | 6.9 | 9.5 | 3.7 | 2.9 | 4.3 |
| MRT [h] | 11.5 | 8.5 | 14.7 | 4.2 | 3.9 | 7.3 |
| $AUC_{0-24}$ [µg * h/ml] | 20.0 | 19.8 | 17.4 | 10.4 | 8.4 | 7.0 |

The improved consumption acceptance of the compound from Example 1 according to the invention compared with enrofloxacin was demonstrated by feeding to young pigs weighing 20 kg in a dosage of 150 ppm. While the animals refuse consumption of enrofloxacin-containing food in dosages of only 50 ppm, the substance according to the invention was eaten without residue within 15 minutes without problems.

Preparation of the Active Compounds

EXAMPLE 1

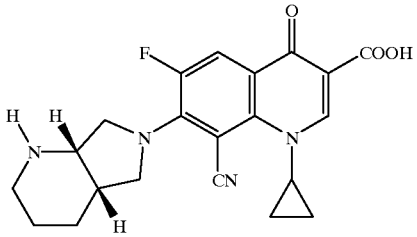

8-Cyano-1-cyclopropyl-7-((1S,6S)-2,8-diazabicyclo [4.3.0]nonan-8-yl)-6-fluoro-1,4-dihydro-4-oxo-3-quinolinecarboxylic acid 690 mg (2.25 mmol) of 7-chloro-8-cyano-1-cyclopropyl-6-fluoro-1,4-dihydro-4-oxo-3-quinolinecarboxylic acid are stirred with 312 mg (2.47 mmol) of (1S,6S)-2,8-diazabicyclo[4.3.0]nonane and 504 mg (4.50 mmol) of 1,4-diazabicyclo[2.2.2]-octane (DABCO) in a mixture of 6.6 ml of dimethylformamide and 6.6 ml of acetonitrile at room temperature overnight. All the volatile components are removed in vacuo, the residue is taken up in water and the resulting solution is brought to pH 7 with dilute hydrochloric acid. The precipitate formed is filtered off with suction, the filtrate is extracted with methylene chloride and the combined organic phases are dried with sodium sulfate and concentrated in vacuo.

Yield: 650 mg (73%)

Melting point: 246–248° C. (decomposition)

EXAMPLE 2

8-Cyano-1-1-cyclopropyl-7-((1S,6S)-2,8-diazabicyclo[4.3.0]nonan-8-yl)-6-fluoro-1,4-dihydro-4-oxo-3-quinolinecarboxylic acid hydrochloride 5.00 g (12.6 mmol) of 8-cyano-1-cyclopropyl-7-((1S,6S)-2,8-diazabicyclo[4.3.0]-nonan-8-yl)-6-fluoro-1,4-dihydro-4-oxo-3-quinolinecarboxylic acid are stirred in 95 ml of 4 N hydrochloric acid/dioxane (1:1) at 60° C. for two hours. The reaction mixture is concentrated in vacuo and the residue is recrystallized from ethanol.

Yield: 4.45 g (82% of theory)

Melting point: 280° C. (with decomposition)

EXAMPLE 3

8-Cyano-1-cyclopropyl-7-((1S,6S)-2,8-diazabicyclo [4.3.0]nonan-8-yl)-6-fluoro-1,4-dihydro-4-oxo-3-quinolinecarboxylic acid mesylate 250 mg (0.63 mmol) of 8-cyano-1-cyclopropyl-7-((1S, 6S)-2,8-diazabicyclo[4.3.0]-nonan-8-yl)-6-fluoro-1,4-dihydro-4-oxo-3-quinolinecarboxylic acid are dissolved in 2 ml of water, and one equivalent of methanesulfonic acid is added. The solution is stirred at room temperature for 30 minutes and then poured onto 20 ml of ethanol. The resulting precipitate is filtered off with suction and then dried.

Yield: 201 mg (65% of theory)

Melting point: 118–124° C.

EXAMPLE 4

8-Cyano-1-cyclopropyl-7-((1S,6S)-2,8-diazabicyclo [4.3.0]nonan-8-yl)-6-fluoro-1,4-dihydro-4-oxo-3-quinolinecarboxylic acid tosylate 250 mg (0.63 mmol) of 8-cyano-1-cyclopropyl-7-((1S, 6S)-2,8-diazabicyclo[4.3.0]-nonan-8-yl)-6-fluoro-1,4- dihydro-4-oxo-3-quinolinecarboxylic acid are dissolved in 2 ml of water, and one equivalent of toluenesulfonic acid is added. The solution is stirred at room temperature for 30 minutes and then poured onto 20 ml of ethanol. The resulting precipitate is filtered off with suction and then dried.

Yield: 309 mg (86% of theory)
Melting point: 222–230° C.

EXAMPLE 5

8-Cyano-1-cyclopropyl-7-((1S,6S)-2,8-diazabicyclo[4.3.0]nonan-8-yl)-6-fluoro-1,4-dihydro-4-oxo-3-quinolinecarboxylic acid trifluoroacetate 200 mg (0.50 mmol) of 8-cyano-1-cyclopropyl-7-((1S,6S)-2,8-diazabicyclo[4.3.0]-nonan-8-yl)-6-fluoro-1,4-dihydro-4-oxo-3-quinolinecarboxylic acid are suspended in 3 ml of ethanol, and one equivalent of trifluoroacetic acid is added. The solution formed is heated under reflux for 30 minutes and then cooled. The resulting precipitate is filtered off with suction and washed with ether.

Yield: 208 mg (81% of theory)
Melting point: 170–178° C.

EXAMPLE 6

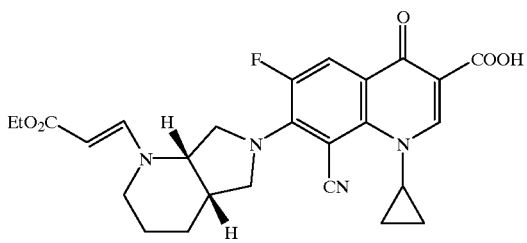

8-Cyano-1-cyclopropyl-7-[(1S,6S)-2-(2-ethloxycarbonyl-vinyl)2,8-diazabicyclo[4.3.0]nonan-8-yl-]6-fluoro-1,4-dihydro-4-oxo-3-quinolinecarboxylic acid 400 mg (1.01 mmol) of 8-cyano-1-cyclopropyl-7-((1S,6S)-2,8-diazabicyclo[4.3.0]-nonan-8-yl)-6-fluoro-1,4-dihydro-4-oxo-3-quinolinecarboxylic acid and 1.03 ml (10.1 mmol) of ethyl propiolate are heated at 120° C. in 7.5 ml of methylglycol for 1 hour. The reaction solution is concentrated in vacuo and the residue is stirred with water and filtered off with suction. The resulting crude product is recrystallized from ethanol.

Yield: 302 mg (61% of theory)
Melting point: 180–182° C.

EXAMPLE 7

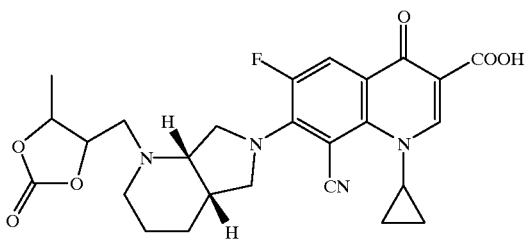

8-Cyano-1-cyclopropyl-7-[(1S,6S)-2-(5-methyl-2-oxo-1,3-dioxol-4-yl)methyl-2,8-diazabicyclo[4.3.0]nonan-8-yl)-6-fluoro-1,4-dihydro-4-oxo-3-quinolinecarboxylic acid 100 mg (0.25 mmol) of 8-cyano-1-cyclopropyl-7-((1S,6S)-2,8-diazabicyclo[4.3.0]-nonan-8-yl)-6-fluoro-1,4-dihydro-4-oxo-3-quinolinecarboxylic acid, 59 mg (0.30 mmol) of 4-bromomethyl-5-methyl-1,3-dioxol-2-one and 30 mg of potassium bicarbonate are heated at 140° C. in 2 ml of dimethylformamide for 30 minutes. The reaction solution is concentrated in vacuo, the residue is taken up in methylene chloride and the mixture is washed with water. The organic phase is dried over magnesium sulfate and concentrated in vacuo. The resulting residue is stirred with water, filtered off with suction and dried.

Yield: 99 mg (77% of theory)
Melting point: 175° C. (with decomposition)

EXAMPLE 8

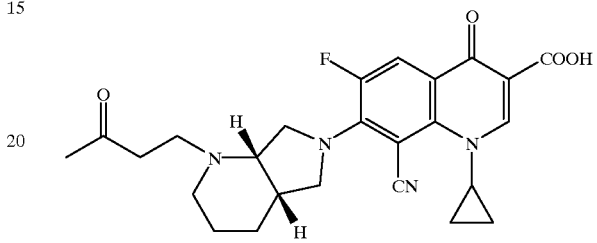

8-Cyano-1-cyclopropyl-7-[(1S,6S)-2-(3-oxo-butyl)-2,8-diazabicyclo[4.3.0]nonan-8-yl]-6-fluoro-1,4-dihydro-4-oxo-3-quinolinecarboxylic acid 300 mg (0.76 mmol) of 8-cyano-1-cyclopropyl-7-((1S,6S)-2,8-diazabicyclo[4.3.0]-nonan-8-yl)-6-fluoro-1,4-dihydro-4-oxo-3-quinolinecarboxylic acid and 0.63 ml (7.6 mmol) of methly vinyl ketone are heated under reflux in 5 ml of methylglycol for 2 hours. The reaction solution is concentrated in vacuo and the residue is stirred with water and filtered off with suction.

Yield: 245 mg (69% of theory)
Melting point: 158–160° C.

EXAMPLE 9

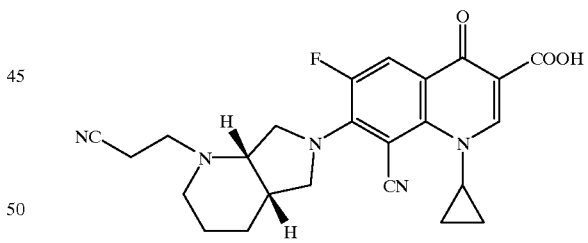

8-Cyano-1-cyclopropyl-7-[(1S,6S)-2-(2-cyanoethyl)-2,8-diazabicyclo-[4.3.0]nonan-8-yl-6-fluoro-1,4-dihydro-4-oxo-3-quinolinecarboxylic acid 400 mg (1.01 mmol) of 8-cyano-1-cyclopropyl-7-((1S,6S)-2,8-diazabicyclo[4.3.0]-nonan-8-yl)-6-fluoro-1,4-dihydro-4-oxo-3-quinolinecarboxylic acid and 1.03 ml (10.1 mmol) of acrylonitrile are heated at 120° C. in 7.5 ml of methylglycol for 1 hour. The reaction solution is concentrated in vacuo and the residue is stirred with water and filtered off with suction. The resulting crude product is recrystallized from ethanol.

Yield: 136 mg (91% of theory)
Melting point: 250° C.

EXAMPLE 10

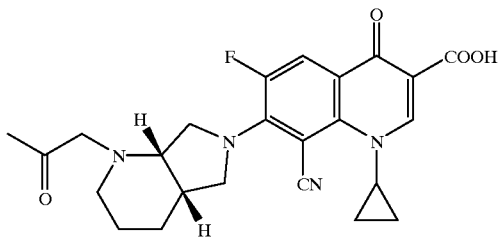

8-Cyano-1-cyclopropyl-7-[(1S,6S)-2-(2-oxypropyl)-
2,8-diazabicyclo4.3.0]nonan-8-yl]-6-fluoro-1,4-
dihydro-4-oxo-3-quinolinecarboxylic acid The title compound is obtained analogously to Example 7 by reaction with chloroacetone.

Melting point: 74–75° C.

EXAMPLE 11

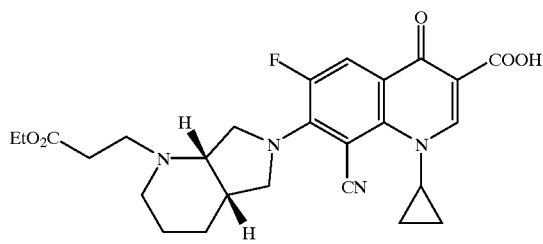

8-Cyano-1-cyclopropyl-7-[(1S,6S)-2-(2-
ethoxycarbonyl-ethyl)-2,8-diazabicyclo-[4.3.0]
nonan-8-yl]-6-fluoro-1,4-dihydro-4-oxo-3-
quinolinecarboxylic acid The title compound is obtained analogously to Example 8 by reaction with ethyl acrylate.

Melting point: 148–150° C.

EXAMPLE 12

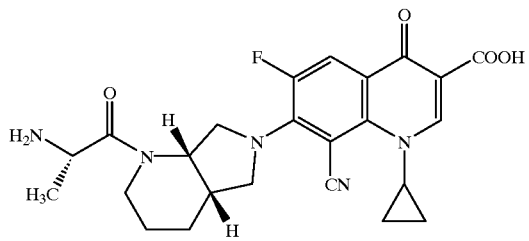

8-Cyano-1-cyclopropyl-7-[(1S,6S)-2-((S)-alanyl)-2,
8-diazabicyclo[4.3.0]nonan-8-yl]-6-fluoro-1,4-
dihydro-4-oxo-3-quinolinecarboxylic acid
hydrochloride 250 mg (0.63 mmol) of 8-cyano-1-cyclopropyl-7-((1S,6S)-2,8-diazabicyclo[4.3.0]-nonan-8-yl)-6-fluoro-1,4-dihydro-4-oxo-3-quinolinecarboxylic acid, 150 mg (0.69 mmol) of N-tert-butyloxycarbonyl-L-alanine-N-carboxyanhydride and 12.5 mg of N,N-dimethylaminopyridine are dissolved in 7.5 ml of dimethylformamide. The solution is stirred at room temperature for 3 hours and then concentrated in vacuo. 20 ml of 4 N hydrochloric acid/dioxane (1:1) are added to the residue and the mixture is heated at 60° C. for 3 hours. The reaction mixture is concentrated in vacuo and the resulting residue is then recrystallized from acetonitrile.

Yield: 164 mg (52% of theory)

Melting point: 245° C. (with decomposition)

EXAMPLE 13

8-Cyano-1-cyclopropyl-7-[(1S,6S)-2-((R)-alanyl)-2,
8-diazabicyclo[4.3.0]nonan-8-yl]-6-fluoro-1,4-
dihydro-4-oxo-3-quinolinecarboxylic acid
hydrochloride The title compound is obtained analogously to Example 12 by reaction with N-tert-butyloxycarbonyl-D-alanine N-carboxyanhydride. Melting point: 213° C. (with decomposition)

EXAMPLE 14

8-Cyano-1-cyclopropyl-7-[(1S,6S)-2-((S)-valinyl)-2,
8-diazabicyclo[4.3.0]nonan-8-yl-6-fluoro-1,4-
dihydro-4-oxo-3-quinolinecarboxylic acid
hydrochloride The title compound is obtained analogously to Example 12 by reaction with N-tert-butyloxycarbonyl-L-valine N-carboxyanhydride.

Melting point: 255° C. (with decomposition)

EXAMPLE 15

8-Cyano-1-cyclopropyl-7-[(1S,6S)-2-((S)-
phenylalanyl)-2,8-diazabicyclo4.3.0]-nonan-8-yl-6-
fluoro-1,4-dihydro-4-oxo-3-quinolinecarboxylic acid
hydrochloride The title compound is obtained analogously to Example 12 by reaction with N-tert-butyloxycarbonyl-L-phenylalanine N-carboxyanhydride.

Melting point: 230° C. (with decomposition)

EXAMPLE 16

8-Cyano-1-cyclopropyl-7-[(1S,6S)-2-((S)-leucinyl)-
2,8-diazabicyclo[4.3.0]nonan-8-yl]-6-fluoro-1,4-
dihydro-4-oxo-3-quinolinecarboxylic acid
hydrochloride The title compound is obtained analogously to Example 12 by reaction with N-tert-butyloxycarbonyl-L-leucine N-carboxyanhydride.

Melting point: 270–274° C. (with decomposition)

EXAMPLE 17

Methyl 8-cyano-1-cyclopropyl-7-[(1S,6S)-2,8-diazabicyclo[4.3.0]nonan-8-yl]-6-fluoro-1,4-dihydro-4-oxo-3-quinolinecarboxylate

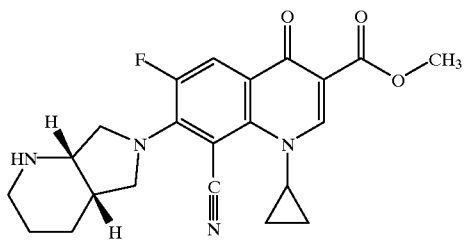

200 mg (0.625 mmol) of methyl 8-cyano-1-cyclopropyl-7-chloro-6-fluoro-1,4-dihydro-4-oxo-3-quinolinecarboxylate, 86 mg (0.683 mmol) of (1S,6S)-2,8-diazabicyclo[4.3.0]nonane and 150 mg (1.34 mmol) of 1,4-diazabicyclo[2.2.2]-octane are stirred in 6 ml of acetonitrile at room temperature for 48 hours. Thereafter, the mixture is evaporated and the residue is partitioned between 15 ml of chloroform and 20 ml of saturated sodium carbonate solution. The organic phase is separated off, the aqueous phase is extracted again with chloroform and, after drying with sodium sulfate, the combined extracts are evaporated. For purification, the residue is chromatographed over silica gel with ethyl acetate/ethanol/25% strength aqueous ammonia solution.

Yield: 140 mg

Melting point: 231°C. (with decomposition)

EXAMPLE 18

Ethyl 8-cyano-1-cyclopropyl-7-[(1S,6S)-2,8-diazabicyclo[4.3.0]nonan-8-yl]-6-fluoro-1,4-dihydro-4-oxo-3-quinolinecarboxylate

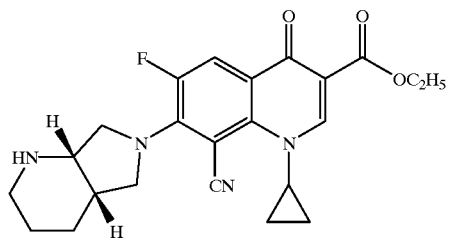

14.32 g (45 mmol) of ethyl 8-cyano-1-cyclopropyl-6,7-difluoro-1,4-dihydro-4-oxo-3-quinolinecarboxylate, 6.31 g (50 mmol) of (1S,6S)-2,8-diazabicyclo[4.3.0]nonane and 10.22 g (101 mmol) of triethylamine are boiled under reflux in 270 ml of acetonitrile for 4 hours. The reaction mixture is left to stand at room temperature for some hours and the solid which has crystallized out is filtered off with suction, rinsed with acetonitrile and dried. 15.6 g of a beige solid are obtained (82% of theory).

Melting point: 209 to 210° C.

EXAMPLE 19

8-Cyano-1-cyclopropyl-7-[(1S,6S)-2,8-diazabicyclo4.3.0]nonan-8-yl]-6-fluoro-1,4-dihydro-4-oxo-3-quinolinecarboxylic acid sodium salt

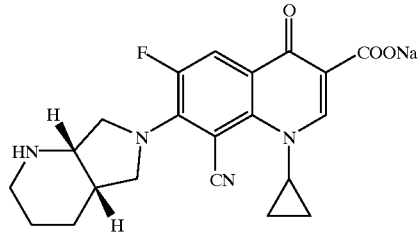

2.12 g (5 mmol) of ethyl 8-cyano-1-cyclopropyl-7-[(1S,6S)-2,8-diazabicyclo-[4.3.0]nonan-8-yl]-6-fluoro-1,4-dihydro-4-oxo-3-quinolinecarboxylate and 0.21 g (5.2 mmol) of sodium hydroxide are heated under reflux in 10 ml of ethanol for 2 hours. Most of then ethanol is then stripped off in vacuo. The residue is topped up with hexane and the resulting solid is filtered off with suction and dried. 2.07 g of a beige solid are obtained (98.9% of theory).

Melting point: 235° C. (with decomposition)

EXAMPLE 20

Ethyl 8-Cyano-1-cyclopropyl-6,7-difluoro-1,4-dihydro-4-oxo-3-quinolinecarboxylate Step a: Methyl 3-Bromo-2,4,5-trifluorobenzoate

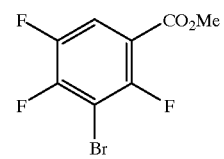

772 g of 3-bromo-2,4,5-trifluoro-benzoyl fluoride are added dropwise to 1460 ml of methanol and 340 g of triethylamin, while cooling with ice. The mixture is stirred at room temperature for 1 hour. The reaction mixture is concentrated in vacuo and the resulting residue is taken up in water and methylene chloride. The water is extracted with methylene chloride once more. The organic phase is dried with $Na_2CO_3$ and concentrated in vacuo. The resulting residue is distilled in vacuo.

Yield: 752,4 g; boiling point: 122° C./20 mbar.

Step b: Methyl 3-Cyano-2,4,5-trifluorobenzoate

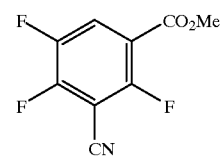

A mixture of 269 g of methyl 3-bromo-2,4,5-trifluorobenzoate, 108 g of copper(I) cyanide and 400 ml of dimethylformainide is heated under reflux for 5 hours. All volatile components are distilled off in vacuo. Fractional distillation of the resulting mixture gives 133 g of the title compound.

Boiling point: 88–89°C./0,0 mbar.

Step c: 3-Cyano-2,4,5-trifluoro-benzoic acid

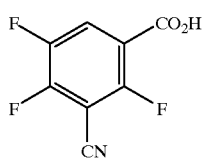

A solution of 156 g of methyl 3-cyano-2,4,5-trifluoro-benzoate in a mixture of 960 ml of glacial acetic acid, 140 ml of water and 69 ml of concentrated sulphuric acid is heated to reflux for 8 hours. The acetic acid is distilled off and the resulting residue is treaten with water. The precipitate is filtered off with suction, washed with water and dried.
Yield: 118,6 g of a white solid.
Melting point: 187–190° C.

Step d: 3-Cyano-2,4,5-trifluoro-benzoyl chloride

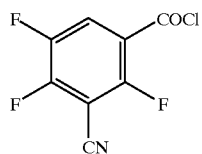

111 g of 3-cyano-2,4,5-trifluoro-benzoic acid, 84 g of oxalyl chloride and a few drops of dimethylformamide in 930 ml of dry methylene chloride are stirred at room temperature for 5 hours. The reaction mixture is concentrated by evaporation and the residue is distilled in vacuo.
Yield 117,6 g of a yellow oil.

Step e: Ethyl 2-(3-Cyano-2,4,5-trifluoro-benzoyl)-3-dimethylamino-acrylate

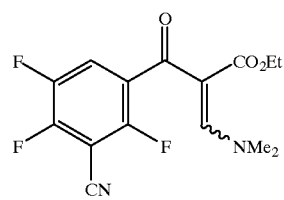

A solution of 55 g of 3-cyano-2,4,5-trifluoro-benzoyl chloride in 50 ml of toluene is added dropwise to a solution of 36,5 g of ethyl 3-dimethylamino-acrylate and 26,5 g of triethylamine in 140 ml of toluene at a temperature between 50 and 55° C. After stirring at 50° C. for 2 hours the reaction mixture is concentrated in vacuo. The crude product is used for the next step without further purification.

Step f: Ethyl 2-(3-Cyano-2,4,5-trifluoro-benzoyl)-3-cyclopropylamino-acrylate

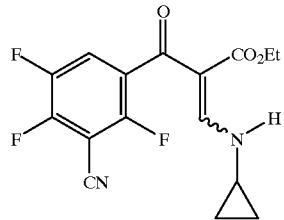

30 g of glacial acetic acid are added dropwise to the crude product from step e at 20° C. Then a solution of 15,75 g of cyclopropylamine in 30 ml of toluene is added dropwise. The reaction mixture is stirred at 30° C. for 1 hour. After the addition of 200 ml of water the mixture is stirred for 15 minutes. The organic phase is separated, extracted with 100 ml of water, dried with $Na_2CO_3$ and concentrated in vacuo. The crude product is used for the next step without further purification.

Step g: Ethyl 8-Cyano-1-cyclopropyl-6,7-difluoro-1,4-dihydro-4-oxo-quinoline-3-carboxylate

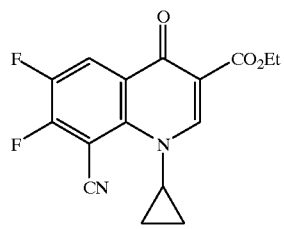

A mixture of the crude product from step f, 27,6 g of $K_2CO_3$, and 80 ml of dimethylformamide are stirred at room temperature for 16 hours. The reaction mixture is poured on 750 ml ice/water and the precipitate is filtered off with suction, washed with 80 ml of cold methanol and dried.
Yield: 47 g of the title compound.
Melting point: 209–211° C.

What is claimed is:

1. The compound methyl-3-cyano-2,4,5-trifluorobenzoate.

2. The compound 3-cyano-2,4,5-trifluorobenzoic acid.

3. The compound 3-cyano-2,4,5-trifluorobenzoyl chloride.

* * * * *